United States Patent
Budayr et al.

[11] Patent Number: 5,587,561
[45] Date of Patent: Dec. 24, 1996

[54] STETHOSCOPE SHIELD

[76] Inventors: Mahdi Budayr, 611 W. Park St., Urbana, Ill. 61801; Jack Kolff, 1086 Franklin St., Johnstown, Pa. 15905

[21] Appl. No.: 508,575

[22] Filed: Jul. 28, 1995

[51] Int. Cl.⁶ ................................. A61B 7/02
[52] U.S. Cl. ............................................. 181/131
[58] Field of Search ........................ 181/131, 137; 381/67; 128/715

[56]  References Cited

U.S. PATENT DOCUMENTS

| | | |
|---|---|---|
| D. 344,798 | 3/1994 | Baskin . |
| 3,213,960 | 8/1964 | Wagner . |
| 3,255,841 | 1/1965 | Hasbrouck . |
| 4,461,368 | 7/1984 | Plourde . |
| 4,867,265 | 9/1989 | Wright . |
| 4,871,046 | 10/1989 | Turner . |
| 5,269,314 | 12/1993 | Kendall et al. . |
| 5,365,023 | 11/1994 | Lawton . |
| 5,424,495 | 6/1995 | Wurzburger .............. 181/131 |

*Primary Examiner*—Khanh Dang
*Attorney, Agent, or Firm*—Thorpe, North & Western

[57] ABSTRACT

A stethoscope shield and method for using the same are disclosed. The shield comprises a generally planar piece of material which is sound transmissive such that when the material is attached to the head of a stethoscope, the shield allows the user of the stethoscope to hear inside the patient, while simultaneously preventing contact between the head of the stethoscope and the patient. The shield is preferably held in place by a removable adhesive so as to facilitate application and removal of the shield.

14 Claims, 2 Drawing Sheets

STETHOSCOPE SHIELD

BACKGROUND OF THE INVENTION

The present invention relates to a method of shielding a stethoscope to prevent the transmission of disease between patients, and, in particular, to a shield which attaches to a stethoscope head prior to use and is then removed so as to prevent disease transmission between patients on whom the stethoscope is used.

The use of stethoscopes is widespread in the medical community. The stethoscope typically includes a head portion with a diaphragm disposed thereon which is placed against the patient, and a pair of ear pieces in communication with the diaphragm. A health care provider places the ear pieces in his or her ears while applying the diaphragm firmly against the skin of the patient. Due to the sensitivity of the diaphragm, the health care provider is able to hear inside of the patient and thereby diagnose illness or determine that no illness is present. For example, when the diaphragm is placed on the patient's chest, the health care provider can listen to respiration and cardiac functions to determine whether irregularities are occurring.

Unfortunately, by contacting the patient's skin, the stethoscope can become contaminated by microorganisms and other diseases which might be present on the patient. This is especially true of patients who have highly infectious diseases which can be passed by skin contact. Using the same stethoscope for several patients increase the risk that diseases will be passed between them. While sterilization of the stethoscope would prevent most of the transfer of disease, it is extremely impractical to sterilize a stethoscope between each use on a patient. For nurses and other health care professionals working in hospitals and other high capacity situations, sterilizing the stethoscope between each use would be next to impossible.

Because of these concerns, several shields have been developed which fit over the stethoscope head. The shields typically include an elastic retention means to hold the shield on the stethoscope head when in use, and allow changing the shield between each patient. Such shields, however, suffer from several problems. First, several of the shields are awkward to position on the stethoscope. Because many of the shields functionally require to hands to be used to place the shield over the head of the stethoscope, the health care provider must put down the patient's charts, etc., in order to attach the shield.

Second, the shields generally hold to the stethoscope's head by attaching on the side opposite the diaphragm. In such a position, however, there is a significant risk that air will be trapped between the diaphragm and the portion of the shield which will contact the patient. Those skilled in the art will appreciate that air adjacent the diaphragm greatly reduces the ability of the diaphragm to magnify the sounds within the patient's body.

In light of the above, there is a need for a stethoscope shield which is easily attached to and removed from the stethoscope head, and for a stethoscope shield which does not interfere with the functioning of the stethoscope.

SUMMARY OF THE INVENTION

Thus, it is an object of the present invention to provide a stethoscope shield which is easy to attach to the head of a stethoscope.

It is another object of the invention to provide such a shield which prevents the transmission of disease between patients.

It is an additional object of the invention to provide a stethoscope shield which does not interfere with the functioning of the stethoscope.

It is yet another object of the invention to provide such a shield which is inexpensive and easy to use.

The above and other objects of the invention are realized in specific illustrated embodiments of a stethoscope shield including a generally planar piece of material releasably attachable to the head of the diaphragm so that the piece of material is disposed between the diaphragm of the stethoscope and the skin of the patient.

In accordance with one aspect of the invention, a releasable adhesive is used to attach the shield directly to the diaphragm. The adhesive minimizes the risk of air pockets common to other shields and thus, provides little or any decrease in sound quality. The releasable adhesive also enables the health care provider to attach the shield to the diaphragm and to remove the same with a single hand. This enables the health care provider to keep the other hand free to hold patient charts and the like.

In accordance with another aspect of the invention, the releasable adhesive enables a plurality of shields to be placed in a stack. When one is needed, it may be pulled from the stack and applied to the stethoscope. After use, the shield may be simply peeled from the stethoscope and disposed of in the usual manner. The next shield in the stack may then be pulled from the stack and applied to the stack and applied to the stethoscope.

In accordance with another aspect of the invention, the shield may include a flange extending generally upward from the generally planar piece of material, so as to prevent the stethoscope from coming into contact with materials, such as body fluids, which are deeper than the thickness of the piece of material.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
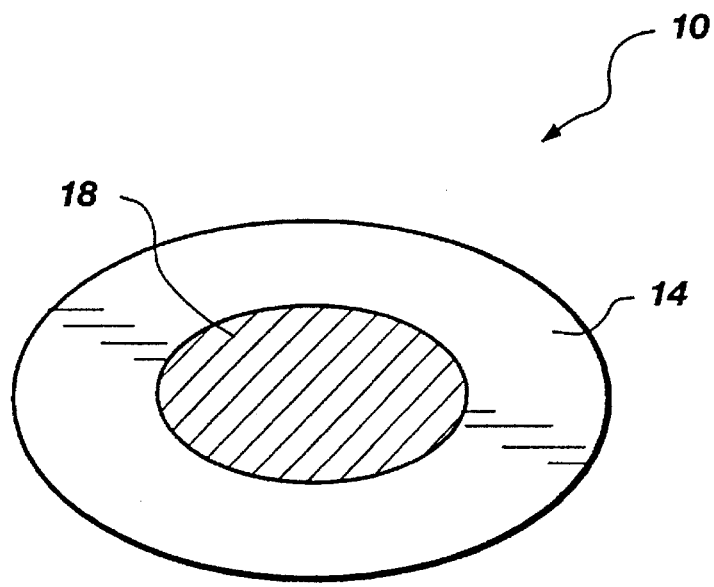
FIG. 1 shows a perspective view of a stethoscope shield made in accordance with the teachings of the present invention.

Referring to FIG. 1, there is shown a stethoscope shield, generally indicated at 10 including a generally planar piece of sound transmissive material 14. The piece of material 14 may be made of numerous difference substances. However, it is anticipated that the piece of material 14 will primarily be made of a thin piece of paper or plastic, or some other material which will not interfere with the transfer of sound between the patient and the stethoscope. Paper and plastic are commonly used materials in the health care profession and are advantageous in that they are both inexpensive and inherently disposable. In order to prevent body fluids from penetrating the shield, a shield made of paper will likely have a thin, fluid impermeable coating such as plastic or wax.

Whatever the substance of the piece of material 14, it is important that it not be readily permeable to microbes and pathogens so as to enable the microbes and pathogens from coming into frequent contact with the head of the stethoscope. If such is not accomplished, the head of the stethoscope can quickly begin to spread disease as it is used on a series of patients.

While shown as being round, the piece of material can be any shape which sufficiently covers the head of the stethoscope to prevent contact between the head and the skin of the patient. It is anticipated that round and square shield 10 will be the most common.

Disposed on the piece of material is an adhesive layer 18 which is used to hold the shield 10 to the head of the stethoscope (not shown). The adhesive layer 18 may be as large as the piece of material 14, or much smaller: as long as it will hold the piece of material to the stethoscope.

The adhesive used will typically be a removable adhesive, such as that used on note pads sold by 3M Corporation under the trademark "POST IT NOTE". As such note pads have become exceedingly common, those skilled in the art will be familiar with numerous adhesives which will releasably hold the piece of material 14 to the stethoscope.

Figure 1A:
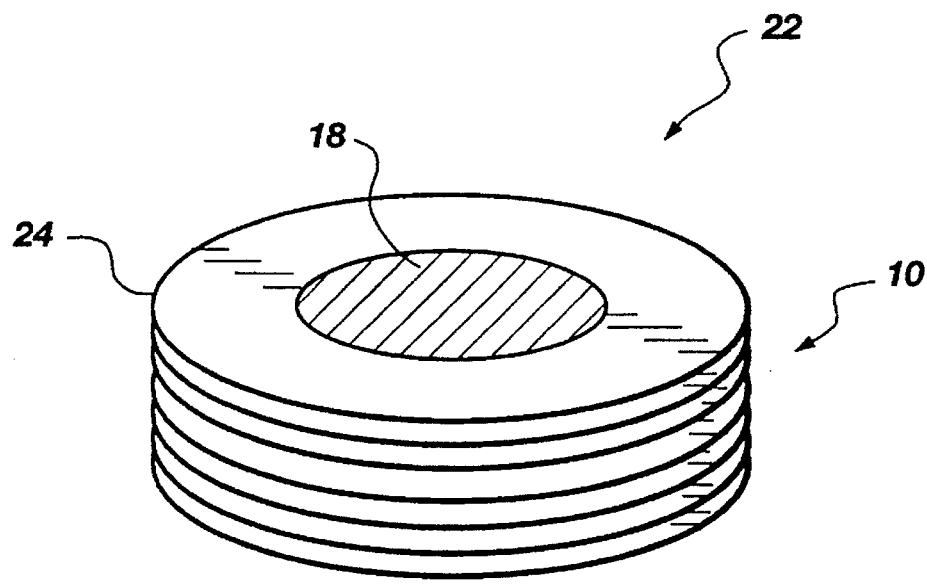
FIG. 1A shows a perspective view of a plurality of shields disposed in a stack.

Referring now to FIG. 1A, there is shown a plurality of shields 10 arranged in a stacked configuration 22. In such an arrangement, a plurality of shields 10 may be held in a very compact arrangement so as to prevent the need for health care providers to repeatedly return to a work station to obtain additional shields.

In order to use a shield 10 from the stack 22, the health care provider would simply place the diaphragm of the stethoscope against the releasable adhesive 18 and apply pressure to ensure attachment. The shield 10 may then be removed from the stack 22 and left on the stethoscope by pulling on a peripheral edge 24 to separate the shield from the next adjacent shield. In such a manner, applying a shield to the stethoscope is no more difficult than removing a "POST IT NOTE" from a stack. Unlike the prior art shields, this can be done easily with one hand, and without putting down patient charts and the like.

Once the shield 10 has been disposed on the stethoscope, the shield may be rubbed against a firm surface to ensure that there are no air bubbles disposed between the shield and the diaphragm of the stethoscope. Those skilled in the art will appreciate that air bubbles significantly decrease the ability of the user to hear inside a patient's body.

Figure 2:
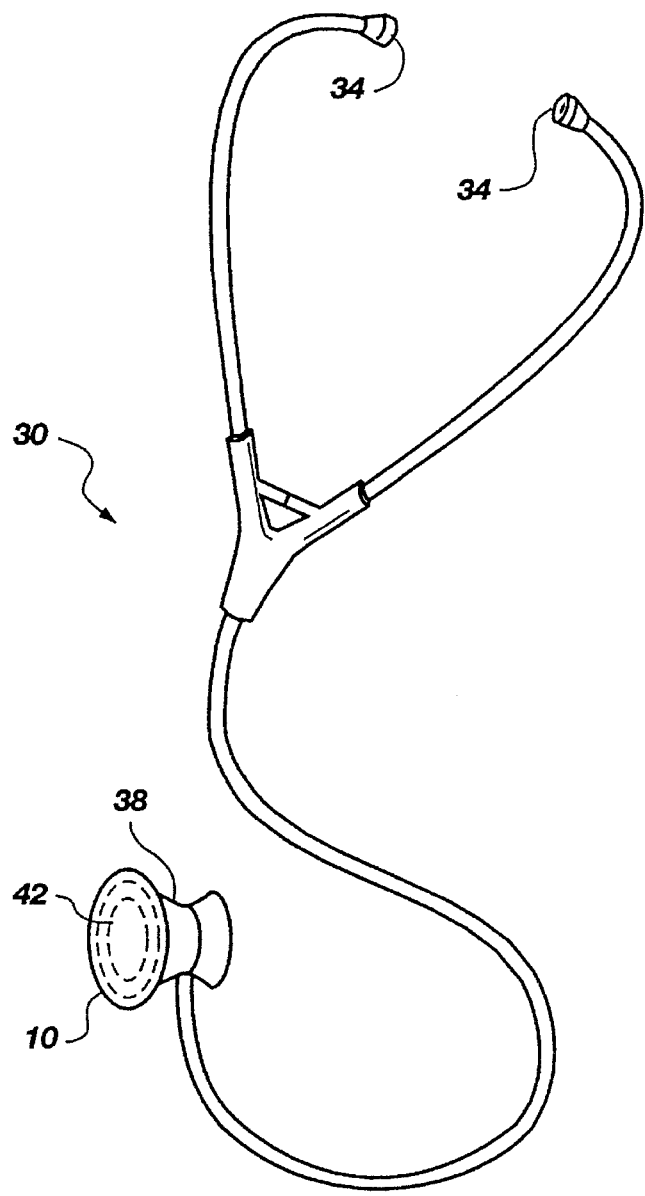
FIG. 2 shows a perspective view of a stethoscope shield attached to a stethoscope in accordance with the teachings of the present invention.

In FIG. 2 there is shown a stethoscope, generally indicated at 30, with a pair of ear pieces 34 which are connected to the head 38. Disposed on the head 38 of the stethoscope 30 is a diaphragm 42. The diaphragm 42 converts vibrations received from the skin of the patient into sounds which may be heard through the ear pieces 34.

A shield 10 is attached to the head 38 by a releasable adhesive so that the shield covers the diaphragm 42. This may be accomplished by adhesively attaching the shield 10 directly to the diaphragm 42, or by attaching the shield to some other portion of the head 38. An advantage arises from attaching the shield 10 directly to the diaphragm 42, as the risk of air being trapped between the shield and the diaphragm is greatly reduced.

Preferentially, the adhesive used to temporarily attach the shield 10 to the head 38 of the stethoscope 30 will be disposed in a thin layer less than 0.01 inches thick. Preferably, the adhesive will be no more than that necessary to hold the shield to the stethoscope. In such a small amount, the adhesive provides very little, if any, disturbance to the diaphragm's sensitivity. Of course, after prolonged usage of the shield's 10, health care personnel may wish to clean the head 38 of the stethoscope to ensure that no residual adhesive builds up on the diaphragm. If allowed to do so, the residual adhesive layer may cause the head 38 of the stethoscope 30 to soil more readily than one without a residue.

Figure 3:
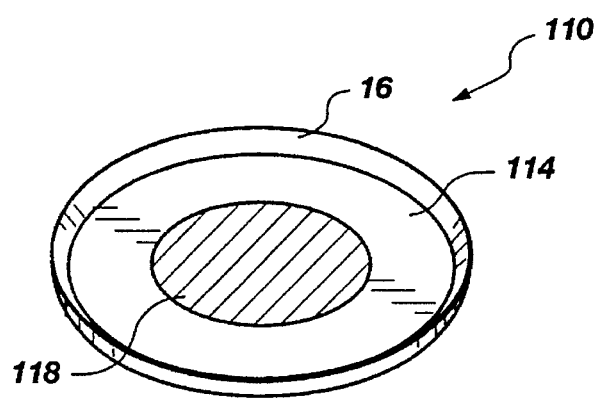
FIG. 3 shows an alternate embodiment of a shield made in accordance with the teachings of the present invention.

Referring now to FIG. 3, there is shown an alternate embodiment of the invention. Rather than being completely planar, as was shield 10 in FIG. 1, the shield 110 includes a generally planar piece of material 114 with a flange 116 disposed about a peripheral portion of the material. The flange 116 extends generally upwardly. Adhesive material 118 is also placed on the piece of material 114 as discussed with respect to FIG. 1.

The flange 116 is used to prevent contamination of the head 38 (FIG. 2) of the microscope 30 (FIG. 2), as is the embodiment discussed in FIGS. 1 through 2. However, the shield 110 is especially adapted for situations in which the head 38 is pressed firmly against the skin, or used on skin which has blood or other bodily fluids present in sufficient quantities that the sides of the head 38 should be protected. The flange 116 provides additional protection for the head 38.

Those skilled in the art will appreciate that the flange 116 may be sloped outwardly so that it is not perpendicular to the plane of the material 114. Even a slight slope enables the shield 110 to be stacked in a similar manner to that shown in FIG. 1A.

Thus there is disclosed a stethoscope shield and a method for using the same. The shield overcomes the disadvantages of the prior art, while being easy to use and inexpensive. Those skilled in the art will be familiar with numerous modifications which may be made without departing from the scope and spirit of the invention. The appended claims are intended to cover such obvious modifications.

What is claimed is:

1. A shield for preventing contact between a diaphragm of a head of a stethoscope and skin of a patient, the shield comprising:

a generally planar piece of material having a surface area larger than the diaphragm of the stethoscope;

an annular flange disposed so as to extend generally upwardly from the planar piece of material, towards the head of the stethoscope so as to shield the head of the stethoscope from body fluids disposed on a patient's skin; and adhesive attachment means applied to the surface of the planar piece of material for removable attachment to the stethoscope at the diaphragm so as to cover the diaphragm of the stethoscope and prevent contact with the skin of a patient.

2. The shield of claim 1, wherein the generally planar piece of material comprises a thin sheet of plastic.

3. The shield of claim 1, wherein the generally planar piece of material comprises a piece of paper.

4. The shield of claim 3, wherein the generally planar piece of material comprises a fluid impermeable layer disposed on the paper so as to prevent penetration of the paper by body fluids.

5. The shield of claim 1, wherein the generally planar piece of material is generally round and has a diameter greater than that of the diaphragm of the head of stethoscope.

6. The shield of claim 1, wherein the planar piece of material comprises a sound transmissive material.

7. The shield of claim 1, wherein the shield comprises a thin layer of removable adhesive disposed thereon.

8. The shield of claim 7, wherein the removable adhesive is disposed so as to attach the shield directly to the diaphragm.

9. A method for shielding the head of a stethoscope from direct contact with the skin of a patient, the head including a diaphragm and the method comprising:

(a) selecting a sound transmissive shield of sufficient size to cover the diaphragm and having an upwardly extending annular flange; and (b) temporarily attaching the shield to the head of the stethoscope with a releasable adhesive so that the annular flange extends adjacent the head of the stethoscope to prevent contact between the diaphragm of the stethoscope and the patient's skin.

10. The method according to claim 9, further comprising placing the shield against the patient's skin so that the diaphragm is disposed on a side of the shield opposite the patient.

11. The method according to claim 9, wherein step (b) comprises, more specifically, forcefully contacting the diaphragm of the stethoscope and adhesive disposed on the shield in order to adhesively attach the shield to the diaphragm.

12. A method for minimizing the transfer of disease between patients, the method comprising the method of claim 9, and further comprising applying force to the shield to remove the shield from the head of the stethoscope after contact with the skin of the patient.

13. The method according to claim 9, wherein step (a) comprises providing a plurality of shields in a stacked arrangement such that one shield is pulled from the stacked shields and attached to the head of the stethoscope, so as to cover the diaphragm of the stethoscope.

14. The method according to claim 13, wherein the stacked shields are temporarily attached to one another by a releasable adhesive.

* * * * *